United States Patent
Dadd et al.

(10) Patent No.: US 8,265,773 B2
(45) Date of Patent: *Sep. 11, 2012

(54) ELECTRODE ASSEMBLY HAVING A FLEXIBLE TIP

(75) Inventors: Fysh Dadd, Lane Cove (AU); Derek Ian Darley, Cromer Heights (AU); Peter Gibson, South Coogee (AU); John Parker, Roseville (AU); Claudiu Treaba, Centennial, CO (US)

(73) Assignee: Cochlear Limited, Macquarie University, NSW (AU)

( * ) Notice: Subject to any disclaimer, the term of this patent is extended or adjusted under 35 U.S.C. 154(b) by 0 days.

This patent is subject to a terminal disclaimer.

(21) Appl. No.: 12/911,433

(22) Filed: Oct. 25, 2010

(65) Prior Publication Data

US 2011/0040364 A1 Feb. 17, 2011

Related U.S. Application Data

(60) Division of application No. 11/604,338, filed on Nov. 27, 2006, now Pat. No. 7,822,487, which is a continuation of application No. 10/149,643, filed as application No. PCT/AU01/01232 on Sep. 28, 2001, now Pat. No. 7,146,227.

(30) Foreign Application Priority Data

| Oct. 4, 2000 | (AU) | PR0541 |
| Oct. 17, 2000 | (AU) | PR0807 |
| Oct. 25, 2000 | (AU) | PR1005 |
| Nov. 29, 2000 | (AU) | PR1778 |

(51) Int. Cl.
*A61N 1/05* (2006.01)

(52) U.S. Cl. .............. 607/137; 607/55; 607/56; 607/57

(58) Field of Classification Search .............. 607/55–57, 607/115–116, 125–126, 136–137
See application file for complete search history.

(56) References Cited

U.S. PATENT DOCUMENTS 3,890,977 A 6/1975 Wilson
(Continued)

FOREIGN PATENT DOCUMENTS

EP 0002068 5/1979
(Continued)

OTHER PUBLICATIONS

Research Disclosure, Nov. 1997, No. 403, p. 785-Article 40342 with Figure 1, "Epicardial-Transvenous Left Atrial Lead with Wound 'Butterfly Tongue' Electrode", Applicant/Inventor Anonymous (Kenneth Mason Publications Ltd, Hampshire, England) Comments on Relevance, Australian Search Report PR 1005.

(Continued)

*Primary Examiner* — Carl H Layno
*Assistant Examiner* — Jessica Sarcione
(74) *Attorney, Agent, or Firm* — Kilpatrick, Townsend & Stockton, LLP.

(57) ABSTRACT

A cochlear implant electrode assembly device comprising an elongate electrode carrier member, a stiffening element, and a stiffening sheath that at least partially envelops the elongate member. The member is made of a resiliently flexible first material and has a plurality of electrodes mounted thereon. The member has a first configuration that allows it to be inserted into an implantee's cochlea. The member also has a second configuration wherein the member is curved to match an inside surface of the cochlea, and at least one intermediate configuration between the first and second configurations. Both the stiffening element and sheath are made of a material that is relatively stiffer than the member. The stiffening element and the stiffening sheath in combination bias the elongate member into the first configuration. If either the stiffening element or the stiffening sheath is removed or deactivated, the elongate member adopts an intermediate configuration.

20 Claims, 2 Drawing Sheets

U.S. PATENT DOCUMENTS

| | | | |
|---|---|---|---|
| 4,033,331 | A | 7/1977 | Guss et al. |
| 4,046,151 | A | 9/1977 | Rose |
| 4,154,247 | A | 5/1979 | O'Neill |
| 4,306,563 | A | 12/1981 | Iwatschenko |
| 4,357,497 | A | 11/1982 | Hochmair et al. |
| 4,381,013 | A | 4/1983 | Dutcher |
| 4,532,930 | A | 8/1985 | Crosby et al. |
| 4,762,135 | A | 8/1988 | van der Puije et al. |
| 4,994,069 | A | 2/1991 | Ritchart et al. |
| 5,025,799 | A | 6/1991 | Wilson |
| 5,554,114 | A | 9/1996 | Wallace et al. |
| 5,571,160 | A | 11/1996 | Nyman |
| 5,645,585 | A | 7/1997 | Kuzma |
| 5,653,742 | A | 8/1997 | Parker et al. |
| 5,755,765 | A | 5/1998 | Hyde et al. |
| 5,762,630 | A | 6/1998 | Bley et al. |
| 5,769,077 | A | 6/1998 | Lindegren |
| 5,782,744 | A | 7/1998 | Money |
| 5,902,329 | A | 5/1999 | Hoffmann et al. |
| 5,957,966 | A | 9/1999 | Schroeppel et al. |
| 5,957,996 | A | 9/1999 | Shiraishi |
| 6,038,484 | A | 3/2000 | Kuzma |
| 6,119,044 | A | 9/2000 | Kuzma |
| 6,195,586 | B1 | 2/2001 | Kuzma |
| 6,304,787 | B1 | 10/2001 | Kuzma et al. |
| 6,309,410 | B1 | 10/2001 | Kuzma et al. |
| 6,421,569 | B1 | 7/2002 | Treaba et al. |
| 6,604,283 | B1 * | 8/2003 | Kuzma ............................ 29/857 |
| 6,968,238 | B1 | 11/2005 | Kuzma |
| 7,050,858 | B1 | 5/2006 | Kuzma et al. |
| 7,146,227 | B2 | 12/2006 | Dadd et al. |
| 7,269,461 | B2 | 9/2007 | Dadd et al. |
| 7,272,449 | B2 | 9/2007 | Dadd et al. |
| 2003/0045921 | A1 | 3/2003 | Dadd et al. |
| 2003/0093139 | A1 | 5/2003 | Gibson et al. |
| 2003/0181967 | A1 | 9/2003 | Dadd et al. |
| 2004/0030376 | A1 | 2/2004 | Gibson et al. |
| 2004/0078057 | A1 | 4/2004 | Gibson |
| 2004/0116995 | A1 | 6/2004 | Dadd |
| 2004/0122501 | A1 | 6/2004 | Dadd et al. |
| 2007/0073371 | A1 | 3/2007 | Dadd et al. |
| 2008/0004684 | A1 | 1/2008 | Dadd et al. |
| 2008/0269864 | A1 | 10/2008 | Dadd et al. |

FOREIGN PATENT DOCUMENTS

| | | |
|---|---|---|
| EP | 0350188 | 1/1990 |
| EP | 0602859 | 6/1994 |
| EP | 0653223 | 5/1995 |
| EP | 0739642 | 10/1996 |
| EP | 0773037 | 5/1997 |
| EP | 0778043 | 6/1997 |
| EP | 0778044 | 6/1997 |
| EP | 0783900 | 7/1997 |
| EP | 0784994 | 7/1997 |
| EP | 0784995 | 7/1997 |
| EP | 0919254 | 6/1999 |
| EP | 0783901 | 4/2003 |
| GB | 2217993 | 11/1989 |
| WO | WO-9710784 | 3/1997 |
| WO | WO-9911321 | 3/1999 |
| WO | WO-9956810 | 11/1999 |
| WO | WO-0033909 | 6/2000 |
| WO | WO-0071063 | 11/2000 |
| WO | WO-0228473 | 4/2002 |
| WO | WO-0228474 | 4/2002 |
| WO | WO-0232498 | 4/2002 |

OTHER PUBLICATIONS

Research Disclosure, Nov. 1997, No. 403, p. 790-Article 0349, p. 791, Figures 1-2, "Epicardial-Transvenous Left Ventricular Lead with Dual Ring Electrodes (Cathode Ring and Anode Ring) Design", Applicant/Inventor Anonymous (Kenneth Mason Publications Ltd, Hampshire, England) Comments on Relevance, Australian Search Report PR 1005.

European Patent Office Communication pursuant to Article 96(2) EPC, issued in connection with European Patent Application No. 01973835.0, May 10, 2004, 3 pages.

European Patent Office Communication under Rule 51(4) EPC, issued in connection with European Patent Application No. 01973835.0, Dec. 21, 2004, 30 pages.

European Patent Office Communication under Rule 51(4) EPC, issued in connection with European Patent Application No. 01973835.0, Feb. 8, 2005, 30 pages.

European Patent Office Communication under Rule 51(4) EPC, issued in connection with European Patent Application No. 01973835.0, Jan. 20, 2005, 30 pages.

European Patent Office Communication under Rule 51(4) EPC, issued in connection with European Patent Application No. 01973835.0, Feb. 25, 2005, 30 Pages.

European Patent Office Decision to Grant a European Patent pursuant to Article 97(2) EPC, issued in connection with European Patent Application No. 01973835.0, Jul. 28, 2005, 2 pages.

European Supplemental Search Report issued in connection with European Patent Application No. 01973835, mailed Jan. 22, 2004. 3 pages.

Communication under Rule 71(3) EPC, issued in connection with European Patent Application No. 01975835.8, Nov. 30, 2009, 31 pages.

European Patent Office, Decision to Grant a European Patent pursuant to Article 97(1) EPC, issued in connection with European Patent Application No. 01975835.8, Apr. 22, 2010, 2 pages.

Supplementary European Search Report, issued in connection with European Patent Application No. 01975835.8, May 15, 2009, 3 pages.

European Patent Office, Supplementary European Search Report, issued in connection with European Patent Application No. 01975875, May 8, 2009, 3 pages.

European Patent Office, Decision to Grant a European Patent pursuant to Article 97(1) EPC, issued in connection with European Patent Application No. 01975875.4, Mar. 25, 2010, 2 pages.

Canadian Intellectual Property Office, Notice of a Requisition by Examiner, issued in connection with Canadian Patent Application No. 2,392,996, Nov. 24, 2008, 3 pages.

Canadian Examiner's Report issued in connection with Canadian Patent Application No. 2,400,729, Nov. 21, 2008, 3 pages.

Translation of a Notice of Reasons for Rejection from the Japanese Patent Office for Japanese Patent in Connection with Japanese Patent Application 2002-535734, 4 pages.

Examiner's First Report, issued in connection with Australian Patent Application No. 93501/01, Aug. 25, 2004, 1 page.

Examiner's First Report, issued in connection with Australian Patent Application No. 95246/01, Aug. 16, 2004, 2 pages.

Examiner's First Report, issued in connection with Australian Patent Application No. 95286/01, Sep. 27, 2004, 1 page.

Notice of Acceptance, issued in connection with Australian Patent Application No. 95286/01, Dec. 20, 2004, 1 page.

International Preliminary Examination Report in connection with International Application No. PCT/AU01/01230, Nov. 27, 2001, 3 pages.

International Search Report in connection with International Application No. PCT/AU01/01230, Oct. 26, 2001, 4 pages.

International Search Report issued in connection with International Application No. PCT/AU01/01231 mailed Oct. 26, 2001, 3 pages.

International Preliminary Examination Report Issued by International Preliminary Examination Authority for the PCT Application No. PCT/AU2001/001231, Nov. 20, 2001, 3 pages.

International Preliminary Examination Report issued by International Preliminary Examination Authority for the PCT Application No. PCT/AU2001/001232, Feb. 25, 2002, 3 pages.

International Search Report issued in connection with International Application No. PCT/AU01/001232 mailed Oct. 26, 2001, 2 pages.

International Preliminary Examination Report issued by International Preliminary Examining Authority in connection with International Patent Application No. PCT/AU2001/001312, Feb. 13, 2002, 4 pages.

International Search Report issued by International Searching Authority in connection with International Patent Application No. PCT/AU2001/001312, Dec. 19, 2001, 3 pages.

Australian Search Report issued in connection with AU Application No. PR 0541, Dec. 20, 2000, 3 pages.

Australian Search Report issued in connection with AU Application No. PR 0542, Dec. 20, 2000, 3 pages.

Australian Search Report issued in connection with AU Application No. PR 0684, Dec. 20, 2000, 3 pages.

Australian Search Report issued in connection with AU Application No. PR 0807, Dec. 20, 2000, 3 pages.

Australian Search Report issued in connection with AU Application No. PR 1005, Dec. 20, 2000, 3 pages.

* cited by examiner

ELECTRODE ASSEMBLY HAVING A FLEXIBLE TIP

CROSS-REFERENCE TO RELATED APPLICATIONS

This application is a Divisional of U.S. patent application Ser. No. 11/604,338, filed on Nov. 27, 2006, now U.S. Pat. No. 7,822,487, entitled "COMBINATION STYLET AND SHEATH FOR AN ELECTRODE ARRAY," which is a Continuation U.S. patent application Ser. No. 10/149,643, filed on May 29, 2003, and entitled "COMBINATION STYLET AND STRAIGHTENING COATING FOR A COCHLEAR IMPLANT ELECTRODE ARRAY," now U.S. Pat. No. 7,146,227, which is a national stage application of International Application No. PCT/AU2001/001232, filed on Sep. 28, 2001, and entitled "COMBINATION STYLET AND STRAIGHTENING COATING FOR A COCHLEAR IMPLANT ELECTRODE ARRAY," which claims priority from Australian Provisional Patent Application No. PS 1778, filed on Novemeber 29, 2000, Australian Provisional Patent Application No. PS 1005, filed on Oct. 25, 2000, Australian Provisional Patent Application No. PS 0807, filed on Oct. 17, 2000, and Australian Provisional Patent Application No. PS 0541, filed on Oct. 4, 2000. Each of these documents is hereby incorporated by reference herein in its entirety.

BACKGROUND

1. Field of the Invention

The present invention relates to an implantable device and, in particular, to an implantable cochlear electrode assembly.

2. Related Art

Hearing loss, which may be due to many different causes, is generally of two types, conductive and sensorineural. Of these types, conductive hearing loss occurs where the normal mechanical pathways for sound to reach the hair cells in the cochlea are impeded, for example, by damage to the ossicles. Conductive hearing loss may often be helped by use of conventional hearing aid systems, which amplify sound so that acoustic information does reach the cochlea and the hair cells.

In many people who are profoundly deaf, however, the reason for deafness is sensorineural hearing loss. This type of hearing loss is due to the absence of, or destruction of, the hair cells in the cochlea which transduce acoustic signals into nerve impulses. These people are thus unable to derive suitable benefit from conventional hearing aid systems, because there is damage to or absence of the mechanism for nerve impulses to be generated from sound in the normal manner.

It is for this purpose that cochlear implant systems have been developed. Such systems bypass the hair cells in the cochlea and directly deliver electrical stimulation to the auditory nerve fibres, thereby allowing the brain to perceive a hearing sensation resembling the natural hearing sensation normally delivered to the auditory nerve. U.S. Pat. No. 4,532,930 provides a description of one type of traditional cochlear implant system.

Cochlear implant systems have typically consisted of two key components, namely an external component commonly referred to as a processor unit, and an implanted internal component commonly referred to as a stimulator/receiver unit. Traditionally, both of these components have cooperated together to provide the sound sensation to an implantee.

The external component has traditionally consisted of a microphone for detecting sounds, such as speech and environmental sounds, a speech processor that converts the detected sounds and particularly speech into a coded signal, a power source such as a battery, and an external antenna transmitter coil.

The coded signal output by the speech processor is transmitted transcutaneously to the implanted stimulator/receiver unit situated within a recess of the temporal bone of the implantee. This transcutaneous transmission occurs through use of an inductive coupling provided between the external antenna transmitter coil which is positioned to communicate with an implanted antenna receiver coil provided with the stimulator/receiver unit. This communication serves two essential purposes, firstly to transcutaneously transmit the coded sound signal and secondly to provide power to the implanted stimulator/receiver unit. Conventionally, this link has been in the form of a radio frequency (RF) link, but other such links have been proposed and implemented with varying degrees of success.

The implanted stimulator/receiver unit typically included the antenna receiver coil that receives the coded signal and power from the external processor component, and a stimulator that processes the coded signal and outputs a stimulation signal to an intracochlea electrode assembly which applies the electrical stimulation directly to the auditory nerve producing a hearing sensation corresponding to the original detected sound.

The external componentry of the cochlear implant has been traditionally carried on the body of the implantee, such as in a pocket of the implantee's clothing, a belt pouch or in a harness, while the microphone has been mounted on a clip mounted behind the ear or on a clothing lapel of the implantee.

More recently, due in the main to improvements in technology, the physical dimensions of the speech processor have been able to be reduced allowing for the external componentry to be housed in a small unit capable of being worn behind the ear of the implantee. This unit has allowed the microphone, power unit and the speech processor to be housed in a single unit capable of being discretely worn behind the ear, with the external transmitter coil still positioned on the side of the user's head to allow for the transmission of the coded sound signal from the speech processor and power to the implanted stimulator unit.

Together with improvements in available technology much research has been undertaken in the area of understanding the way sound is naturally processed by the human auditory system. With such an increased understanding of how the cochlea naturally processes sounds of varying frequency and magnitude, there is a need to provide an improved cochlear implant system that delivers electrical stimulation to the auditory nerve in a way that takes into account the natural characteristics of the cochlea.

It is known in the art that the cochlea is tonotopically mapped. In other words, the cochlea can be partitioned into regions, with each region being responsive to signals in a particular frequency range. This property of the cochlea is exploited by providing the electrode assembly with an array of electrodes, each electrode being arranged and constructed to deliver a cochlea-stimulating signal within a preselected frequency range to the appropriate cochlea region. The electrical currents and electric fields from each electrode stimulate the cilia disposed on the modiolus of the cochlea. Several electrodes may be active simultaneously.

It has been found that in order for these electrodes to be effective, the magnitude of the currents flowing from these electrodes and the intensity of the corresponding electric fields, are a function of the distance between the electrodes and the modiola. If this distance is relatively great, the threshold current magnitude must be larger than if the distance is relatively small. Moreover, the current from each electrode may flow in all directions, and the electrical fields corresponding to adjacent electrodes may overlap, thereby causing cross-electrode interference. In order to reduce the threshold stimulation amplitude and to eliminate cross-electrode interference, it is advisable to keep the distance between the electrode array and the modiola as small as possible. This is best accomplished by providing the electrode array in the shape which generally follows the shape of the modiola. Also, this way the delivery of the electrical stimulation to the auditory nerve is most effective as the electrode contacts are as close to the auditory nerves that are particularly responsive to selected pitches of sound waves.

In order to achieve this electrode array position close to the inside wall of the cochlea, the electrode needs to be designed in such a way that it assumes this position upon or immediately following insertion into the cochlea. This is a challenge as the array needs to be shaped such that it assumes a curved shape to conform with the shape of the modiola and must also be shaped such that the insertion process causes minimal trauma to the sensitive structures of the cochlea. In this sense it has been found to be desirable for the electrode array be generally straight during the insertion procedure.

Several procedures have been adopted to provide an electrode assembly that is relatively straightforward to insert while adopting a curved configuration following insertion in the cochlea. In one case, a platinum wire stylet is used to hold a pre-curved electrode array in a generally straight configuration up until insertion. Following insertion, the platinum stylet is withdrawn allowing the array to return to its pre-curved configuration. While such an arrangement has proved beneficial, penetration of the wall of the cochlea is possible if the surgeon does not insert the array using an appropriate rate and orientation, or withdraw the stylet at the appropriate end point during insertion of the assembly.

In another development, a bimetallic filament (such as nickel/titanium) or a shape memory alloy (eg. an alloy of nickel and titanium) is positioned in the electrode assembly and used to again hold a pre-curved electrode array in a generally straight configuration while the array is at about room temperature. On insertion into the body and exposure to body temperature, the alloy or filament bends into a preselected curved configuration.

In a still further arrangement, a longitudinal element that is arranged on one side of the array and constructed to change its dimension on insertion can be utilised. For example, the longitudinal element could include a hydrogel, such as polyacrylic acid (PAA) or polyvinyl alcohol (PVA), which expands after insertion by absorbing water from the cochlear fluid.

In developing such electrode array designs, it is of great importance that the design be constructed to minimise potential damage to sensitive structures in the cochlea on insertion and placement. For example, in the case of use of platinum stylets, some studies suggest that wall penetration is a problem in about 20% of cases. Each of the above constructions suffer from a number of disadvantages in this regard.

The present invention is directed to an electrode assembly adapted to overcome some of the difficulties of prior art electrode assemblies.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY

In one aspect of the invention, an electrode assembly for an implantable hearing prosthesis is disclosed. The implantable hearing prosthesis comprises an elongate member formed from a resiliently flexible material and having a plurality of electrodes mounted thereon, a tip disposed at a distal end of the elongate member, wherein the tip is formed from one or more materials that collectively are relatively less stiff than the elongate member, and a stiffening sheath configured to surround the tip, wherein the stiffening sheath is formed from a material that is stiffer than the tip region.

In another aspect of the present invention, an implantable tissue-stimulating device is disclosed. The implantable tissue-stimulating device comprises an electrode assembly. The electrode assembly comprises an elongate member formed from a resiliently flexible material and having a plurality of electrodes mounted thereon, a tip disposed at a distal end of the elongate member, wherein the tip is formed from one or more materials that collectively are relatively less stiff than the elongate member, and a stiffening sheath configured to surround the tip, wherein the stiffening sheath is formed from a material that is stiffer than the tip region.

In yet another aspect of the present invention, an implantable hearing prosthesis is disclosed. The implantable hearing prosthesis comprises an electrode assembly. The electrode assembly comprises an elongate member formed from a resiliently flexible material and having a plurality of electrodes mounted thereon, a tip disposed at a distal end of the elongate member, wherein the tip is formed from one or more materials that collectively are relatively less stiff than the elongate member, and a stiffening sheath configured to surround the tip, wherein the stiffening sheath is formed from a material that is stiffer than the tip region.

BRIEF DESCRIPTION OF THE DRAWINGS

By way of example only, preferred embodiments of the invention are now described with reference to the accompanying drawings, in which.

DETAILED DESCRIPTION

One embodiment of a cochlear implant electrode assembly according to the present invention is depicted generally as 10 in the drawings.

The depicted electrode assembly 10 has an electrical lead extending back to a stimulator/receiver housing. In considering this invention, it is to be understood that each electrode may have one or more wires (not depicted) electrically connected thereto and extending from each respective electrode back through the lead to the stimulator/receiver.

Figure 1:
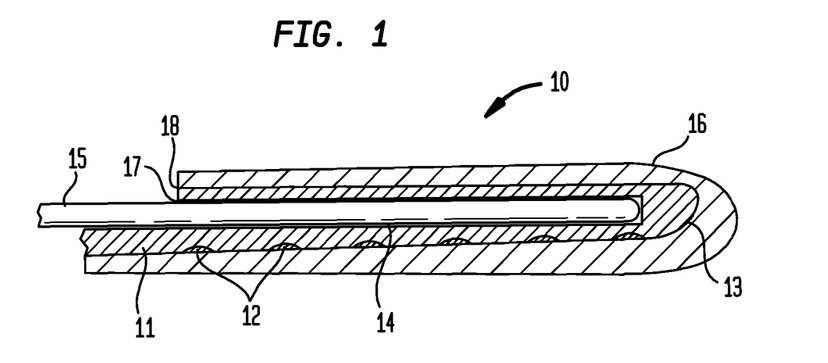
FIG. 1 is a simplified cross-sectional view of one embodiment of an electrode assembly according to the present invention depicted in its first configuration.

The assembly 10 comprises an elongate electrode carrier member 11 having a plurality of electrodes 12 mounted thereon. For the purposes of clarity, the electrodes 12 depicted in FIG. 1 are not necessarily shown to scale.

The depicted elongate member 11 is preformed from a resiliently flexible silicone with memory and is preformed to a curved configuration suitable for insertion in the scala tympani of the cochlea. The elongate member 11 has a first end 13 that is firstly inserted into the cochlea upon insertion of the assembly 10.

Figure 4:
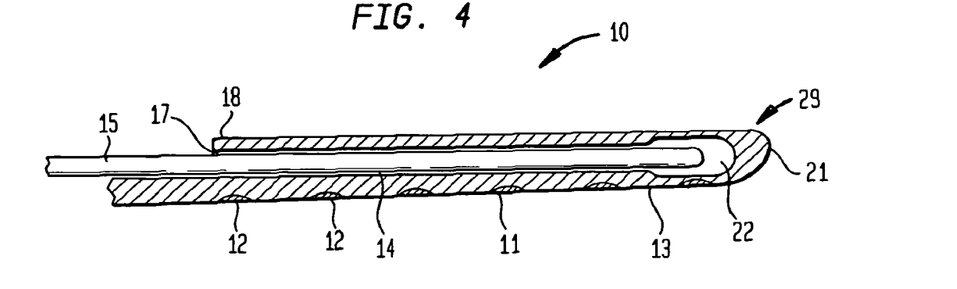
FIG. 4 is a simplified cross-sectional view of another embodiment of an electrode assembly according to the present invention.

As depicted in FIG. 4, the elongate member 11 can have a tip member 29 integrally formed with its first end 13. The tip 29 is formed from the same silicone used to fabricate the elongate member 11 and, in the depicted embodiment, the material of tip member 29 has a resilient flexibility equal to that of the material used for the carrier member 11.

Figure 5A:
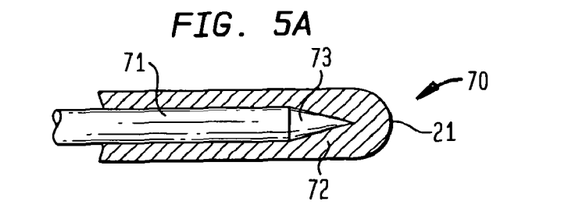
FIGS. 5a-5d depict alternative tip structures for the electrode assembly depicted in FIG. 4.

Possible alternative constructions for the tip member 29 are provided in FIGS. 5a-5d. As depicted in FIG. 5a, the tip member 70 can be solid and formed of an inner core 71 of relatively stiff material 71 and an outer layer 72 of relatively flexible material. The core 71 can taper in diameter over region 73 towards the distal end 21. The taper 73 causes the overall stiffness of the tip 70 to increase over the length of the taper 73 away from the distal end 21. The outer layer 72 can be formed of the same material as the remainder of the body of the elongate carrier member 11 or can be a different material.

Figure 5B:
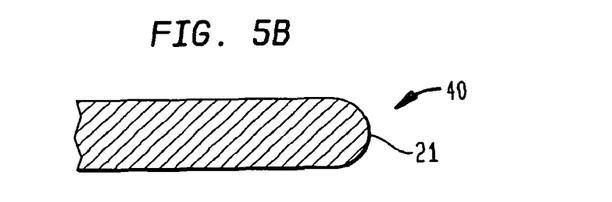

As depicted in FIG. 5b, the tip member 40 can comprise a solid mass integrally formed to the first end 13 of the elongate carrier 11.

Figure 5C:
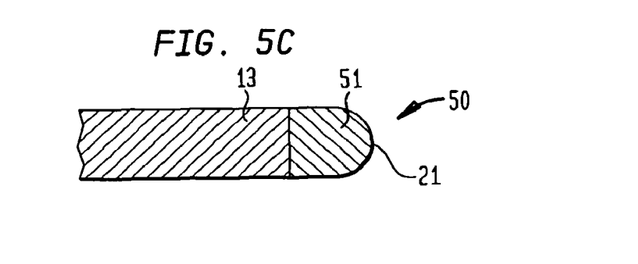

Still further and as depicted in FIG. 5c, the tip member 50 can comprise a solid mass 51 that is formed separately from the carrier member 11 and subsequently adhered thereto.

Figure 5D:
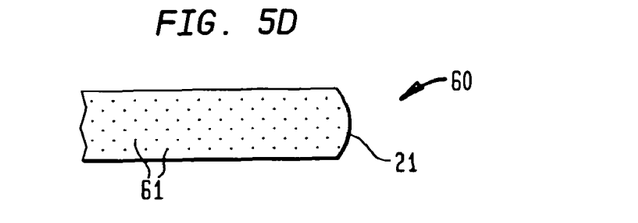

As depicted in FIG. 5d, the tip member 60 can comprise an elastomeric silicone material having a plurality of substantially spherical platinum particles 61 dispersed therethrough. The particles 61 have a diameter between about 50, um and 100 ism. It will be appreciated that the particles 61 depicted in FIG. 6d are not drawn to scale.

In FIG. 5d, the particles 61 are depicted as substantially evenly dispersed through the tip member 60. In another embodiment, the particles could be non-evenly dispersed through the tip member. For example, the particles could increase in density away from the distal end 21 towards the proximal end of the tip member 60. By varying the density of the platinum particles 61, it is possible to vary the relative stiffness of the tip member 60.

In addition to, or instead of, being used to potentially modify the physical characteristics of the tip member, the provision of the metallic particles 61 also result in the tip member 60 being detectable by fluoroscopy and X-ray techniques. This provides another means for the surgeon to either monitor the placement and position of the tip member 60 during or after insertion of the electrode array 10 in an implantee's cochlea.

Disposed within a lumen 14 is a substantially straight platinum stylet 15. The stylet 15 alone has a stiffness that is insufficient to retain the silicone elongate member 11 in a straight configuration.

While a platinum stylet is depicted, a bioresorbable stylet formed from a bioresorbable polyacrylic acid (PAA) that is adapted to dissolve or soften on exposure to cochlear fluids could be utilised with appropriate modification to the elongate carrier member 11. Equally, whilst a substantially cylindrical lumen is depicted, the lumen 14 could indeed be any shape necessary to perform the function. Again, the PAA stylet in this invention has a stiffness insufficient to retain the silicone elongate member 11 in a straight configuration as depicted in FIG. 1. It will be appreciated that a bioresorbable stylet could be formed from other suitable bioresorbable materials. A stylet made from a shape memory alloy or heat sensitive material could also be utilised as a stylet 15.

Overlaying the depicted elongate member 11 is a stiffening sheath 16 of bioresorbable material. The bioresorbable material of the depicted stiffening sheath 16 is PAA that is adapted to dissolve on exposure to cochlear fluids. Other suitable bioresorbable materials can be envisaged and such materials need not necessarily dissolve on exposure to fluids, the current invention could also function correctly if the sheath 16 is made of a material that softens upon exposure to fluids but does not get absorbed.

While the elongate member 11 is manufactured with a preformed curved configuration, the assembly 10 is typically delivered to a surgeon with the stylet 15 and sheath 16 in place. The combination of the stylet 15 and sheath 16 is sufficient to hold the elongate member 11 in the straight configuration depicted in FIG. 1.

Figure 2:
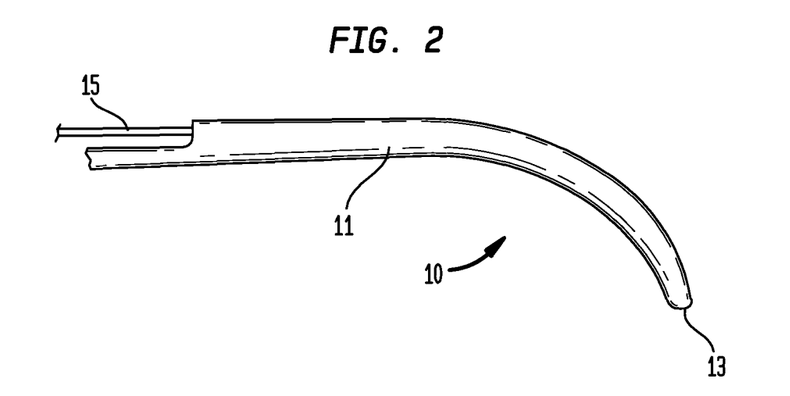
FIG. 2 is a simplified side elevational view of the electrode assembly of FIG. 1 depicted in an intermediate configuration.

On insertion into the scala tympani of the cochlea 30, the cochlear fluids commence to dissolve or soften the sheath 16. As the PAA softens and dissolves, the elongate member 11 commences to re-curl (see FIG. 2) as the stiffness of the stylet 15 is insufficient to hold the elongate member 11 straight. The provision of the stylet 15 within the elongate member 11 does, however, prevent the elongate member 11 from adopting its pre-formed spirally curved configuration.

Figure 3:
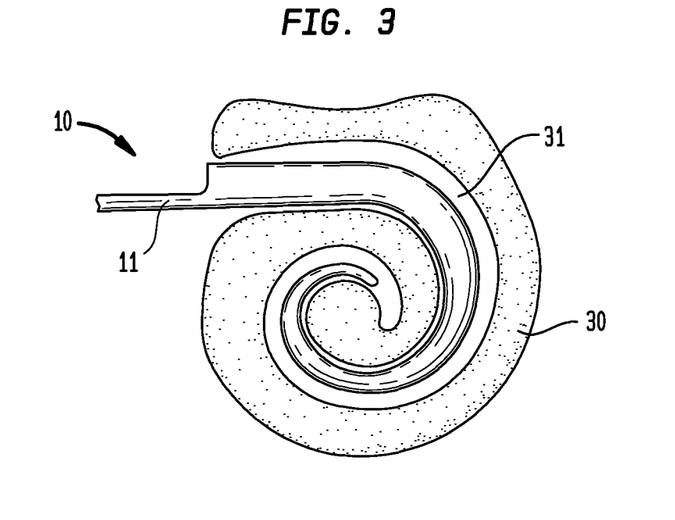
FIG. 3 is a simplified part-sectional, part side elevational view of the electrode assembly depicted in its second configuration following insertion in the cochlea.

As the elongate member 11 curls, the surgeon can continue to further insert the assembly 10 into the scala tympani 31 with a lessened risk of the member 11 puncturing fine tissues of the cochlea 30. It is possible that during the further insertion process the surgeon may simultaneously withdraw the platinum stylet 15 through the opening 17 of the lumen 14 at end 18. On withdrawal of the stylet 15, the elongate member 11 is free to adopt the spiral configuration depicted in FIG. 3 with the electrodes facing the modiola within the cochlea 30 so that they are positioned as close as possible to the spiral ganglia thereof.

It is also envisaged that in one arrangement the surgeon may withdraw the stylet 15 first and rely upon the sheath 16 to maintain the array in the intermediate position.

The combination of the stiffening element 15 and stiffening sheath 16 provides the surgeon with greater control of the implantation procedure for the cochlear implant electrode assembly 10. The provision of greater control minimises the potential for trauma to the sensitive tissues inside the cochlea and also enhances the likelihood of successful placement of the assembly 10 at the first attempt.

While the preferred embodiment of the invention has been described in conjunction with a cochlear implant, it is to be understood that the present invention has wider application to other implantable electrodes, such as electrodes used with pacemakers.

Further Embodiments

According to a first aspect, the present invention is an implantable tissue-stimulating device comprising: an elongate member having a plurality of electrodes mounted thereon and having a first configuration that allows said member to be inserted into an implantee's body, a second configuration wherein said elongate member is adapted to apply a preselected tissue stimulation with the electrodes, and at least one intermediate configuration between said first and second configurations, said elongate member being made of a resiliently flexible first material; a stiffening element made of a material relatively stiffer than said first material; and a stiffening sheath at least partially enveloping said elongate member and made of a material relatively stiffer than said first material; wherein said stiffening element and said stiffening sheath in combination bias said elongate member into said first configuration and further wherein if either the stiffening element or the stiffening sheath is removed or deactivated, the elongate member adopts said at least one intermediate configuration.

In a preferred embodiment, the second configuration of the elongate member is curved. More preferably, the elongate member adopts a spiral configuration when in the second configuration.

According to a second aspect, the present invention is a cochlear implant electrode assembly including: an elongate electrode carrier member having a plurality of electrodes mounted thereon and having a first configuration that allows said member to be inserted into an implantee's cochlea, a second configuration wherein said elongate member is curved to match an inside surface of said cochlea, and at least one intermediate configuration between said first and second configurations, said elongate member being made of a resiliently flexible first material; a stiffening element made of a material relatively stiffer than said first material; and a stiffening sheath at least partially enveloping said elongate member and made of a third material relatively stiffer than said first material; wherein said stiffening element and said stiffening sheath in combination bias said elongate member into said first configuration and further wherein if either the stiffening element or the stiffening sheath is removed or deactivated, the elongate member adopts said at least one intermediate configuration.

The elongate member is preferably preformed from a plastics material with memory and is preformed to the second configuration. The elongate member preferably has a first end that is firstly inserted into the implantee.

In a preferred embodiment, the first configuration is preferably substantially straight. More preferably, the first configuration is straight.

In a preferred embodiment, the elongate member is formed from a suitable biocompatible material. In one embodiment, the material can be a silicone, such as a flexible silicone elastomer-Silastic. Silastic MDX 4-4210 is an example of one suitable silicone for use in the formation of the elongate member. In another embodiment, the elongate member can be formed from a polyurethane.

In a further embodiment, the elongate member can have a resiliently flexible tip member extending forwardly from the first end of the body. The tip member preferably has a distal end and a proximal end. The tip member can have a stiffness that is relatively less stiff than said stiffening element. The tip member can further be formed of a material that is substantially the same or the same stiffness as the body of the elongate member. In another embodiment, the tip member can be formed of a material that is relatively less stiff than at least a portion of the elongate member. In a further embodiment, the tip member can be formed of a material that undergoes a change in stiffness, preferably a decrease in stiffness, on insertion into the body, such as the cochlea.

In a further embodiment, the stiffness of the tip member can vary along at least a portion of its length from its distal end to its proximal end. In one embodiment, the stiffness of the tip member can vary over the entire length of the tip member or only a portion thereof. The stiffness can increase from the distal end to the proximal end. In one embodiment, the stiffness of the tip member over said portion or its length can increase gradually from its distal end towards to the proximal end. The increase in stiffness can be substantially smooth or increase in a stepwise fashion.

In a further embodiment, the tip member can be formed of the same material as the body of the elongate member. In another embodiment, the tip member can be formed of a different material to that of the body of the elongate member. The tip member can be comprised of an inner relatively stiff core of material having a tapered end, with at least the tapered end being overlaid by a relatively flexible material that extends beyond the tapered end of the core material so that the tip member undergoes a gradual decrease in flexibility in the region of the tapered end of the core moving away from the distal end.

The tip member can be formed separately to the body of the elongate member and mounted thereto. For example, the tip member can be adhered to the first end of the body of the elongate member. In another embodiment, the tip member can be integrally formed with the body of the elongate member. The tip member can be formed from a silicone material. In another embodiment, the tip member can be formed of an elastomeric material, such as polyurethane.

In another embodiment, the tip member can have a plurality of metallic particles dispersed therethrough. The metallic particles can be substantially evenly dispersed through the tip member. Alternatively, the metallic particles can be non-evenly dispersed throughout the tip member. In one embodiment, the metallic particles can increase in density away from the distal end towards the proximal end of the tip member. By varying the density of the metallic particles, it is possible to vary the relative stiffness of the tip member.

The metallic particles preferably comprise a biocompatible material, such as platinum. The particles can be substantially spherical or spherical. It will be appreciated that the particles can have other suitable shapes. In one embodiment, the particles can have a diameter between about 50 µm and 100 µm.

In addition to, or instead of, being used to potentially modify the physical characteristics of the tip member, the provision of the metallic particles also result in the tip member being detectable by fluoroscopy and X-ray techniques. This provides another means for the surgeon to monitor the placement and position of the tip member during or after insertion of the electrode array in the body, such as in the cochlea.

When the elongate member is in the first configuration, the tip member is preferably substantially straight and, more preferably, straight.

In a further embodiment, the tip member can be coated with a lubricious material. The lubricious material can be a bioresorbable or non-bioresorbable material.

The tip member can be formed from, or incorporate as a portion thereof, a bioresorbable material. The presence of the bioresorbable material preferably results in the flexibility of the tip member increasing on insertion of the tip member into the body, such as the cochlea. The bioresorbable material in the tip member can be selected from the group consisting of polyacrylic acid (PAA), polyvinyl alcohol (PVA), polylactic acid (PLA) and polyglycolic acid (PGA).

In another embodiment, the tip member can be formed from, or incorporate as a portion thereof, a polymeric coating which becomes softer, and so increases in resilient flexibility, in the presence of moisture or body heat.

The tip member preferably has a length from its distal end to its proximal end in the range of about 0.3 to 4 mm, more preferably about 1.0 to 3 mm. The diameter of the tip member can be substantially constant for a majority of its length or can vary in diameter. The tip member can be substantially cylindrical, cylindrical, or non-cylindrical for a majority of its length. At the distal end, the diameter preferably gradually decreases to form a rounded end. The maximum diameter of the tip member is preferably about 0.55 mm.

In one embodiment, the tip member can be solid. In another embodiment, the tip member can have an external wall defining a cavity. In one embodiment, the cavity can have a diameter greater than that of the receiving portion of the body of the elongate member. In a further embodiment, the cavity can extend from the proximal end towards the distal end of the tip member. The cavity can decrease in diameter away from the proximal end. The cavity can be in communication with a distal end of the receiving portion of the body of the elongate member. In a further embodiment, the stiffening means can extend into the cavity when positioned within the device or assembly according to the respective aspects of the present invention. In a preferred embodiment, the tip member can move relative to the stiffening means when it extends into the cavity of the tip member.

In general, the tip could be made of a combination of materials arranged in a variety of geometries depending on the specific design goal. The outside shape and size of the tip can also be made in a variety of forms depending on the design goal.

In one embodiment, the stiffening element is formed of a bioresorbable material which softens or dissolves on exposure to a fluid. The stiffening element can soften or dissolve on exposure to a saline solution or a body fluid of the implantee, such as cochlear fluid. In a further embodiment, the bioresorbable material of the stiffening element is selected from the group consisting of polyacrylic acid (PAA), polyvinyl alcohol (PVA), polylactic acid (PLA) and polyglycolic acid (PGA). It is envisaged that other similar materials could also be used.

In another embodiment, the stiffening element can be formed from a non-bioresorbable material. In this embodiment, the stiffening element can comprise a metallic stylet, or a stylet from any other suitable stiffening material, extending through a lumen in the elongate member. In one embodiment, the stylet can be formed from a biocompatible material, such as a metal, metallic alloy or a stiff plastic. In a preferred embodiment, a metal stylet can be formed from platinum.

In a still further embodiment, the stiffening element can be formed from a shape memory alloy or a heat sensitive material. For example, the stiffening element can be formed from a nickel/titanium alloy, or a bimetallic element formed of a laminate of two different metals, that is shaped to take a straight or substantially straight configuration at room temperature but bends into another shape once it is exposed to body temperature.

In one embodiment, the lumen for the stylet can be cylindrical and also can have an opening formed therein. In the case of a metal stylet, the stylet can extend out of the opening allowing the stylet to be manipulated and removed from the lumen during or following insertion of the device. In the case of a bioresorbable stiffening element, the opening can act as a fluid ingress means allowing body fluids to enter the lumen on insertion of the device into an implantee.

Where the stiffening element is a metallic or metallic alloy or plastic stylet, the stiffening sheath is preferably formed of a bioresorbable material which dissolves or softens on exposure to a fluid. The stiffening sheath can dissolve or soften on exposure to a saline solution or a body fluid of the implantee, such as cochlear fluid.

In a further embodiment, the bioresorbable material of the stiffening sheath is selected from the group consisting of polyacrylic acid (PAA), polyvinyl alcohol (PVA), polylactic acid (PLA) and polyglycolic acid (PGA). It is also envisaged that other suitable materials could also be used.

The device can include an additional layer surrounding the stiffening sheath. The additional layer can have a first rate of fluid ingress therethrough and have at least one fluid ingress means formed therein, the rate of fluid ingress through the fluid ingress means being greater than the first rate of fluid ingress through the additional layer.

The fluid ingress means can comprise one or more openings in the additional layer. The openings can be closable. The openings can comprise slits in the additional layer. The slits can be formed to allow substantially the same or the same rate of ingress of fluid through the additional layer. In another embodiment, at least one slit can allow a different rate of progress of fluid through the additional layer compared to the other slits.

Where the stiffening element is a metal or bioresorbable stylet, the stiffening sheath can, in one embodiment, be formed from a shape memory alloy or a heat sensitive material. For example, the stiffening sheath can be formed from a nickel/titanium alloy, or a bimetallic element formed of a laminate of two different metals, that is shaped to take and maintain the straight or substantially straight configuration of the elongate member at room temperature but bends it into another shape once it is exposed to body temperature.

While both the stiffening element and the stiffening sheath are in position within the device, it will retain the first configuration, which as discussed is preferably straight. If the stiffening sheath is removed or softened, whether it is by dissolution or otherwise, the remaining stiffening element has insufficient strength to retain the elongate member in its first configuration. It is preferred that the elongate member, on removal or softening of the stiffening sheath, will adopt an intermediate configuration in which the elongate member has at least some curvature.

The purpose of allowing the elongate member to adopt this intermediate configuration is to enable the elongate member to be inserted into the cochlea in a way which minimises trauma to the walls of the cochlea. The preferred shape of this intermediate configuration is for the elongate member to assume a shape that is more curved than the straight configuration present upon insertion. By providing the previously straight array with a more curved shape, the elongate member is guided to adopt a mid-scala trajectory as it is inserted into the cochlea. This ensures that as the elongate member is carefully inserted deeper into the spiral shaped cochlea, the intermediate curved configuration assists in assuring that the elongate member can be inserted deep into the cochlea without causing excessive trauma to the walls of the cochlea.

On subsequent removal of the stiffening element, the elongate member is free to adopt the fully curved second configuration desired of an implant for final position in the cochlea.

The present invention provides a surgeon with a means to at least partially control the rate of curvature formation in a cochlear electrode assembly during insertion into the cochlea. Such increased control is envisaged to reduce the potential for trauma to the cochlea caused by electrode assembly insertion. The present invention also provides a means of assisting the insertion process of the electrode assembly into the cochlea by allowing the electrode assembly to alter its configuration during the insertion process to allow for deeper and more desirable cochlea penetration.

In a further embodiment, at least a portion of an outer surface of the elongate member can have a coating of a lubricious material. In one embodiment, a substantial portion or the entire outer surface of the elongate member can have a coating of the lubricious material.

In this embodiment, the lubricious material can be selected from the group comprising polyacrylic acid (PAA), polyvinyl alcohol (PVA), polylactic acid (PLA) and polyglycolic acid (PGA). It is envisaged that other similar materials could also be used.

In a further aspect, the present invention comprises a method of implanting a tissue-stimulating device or cochlear electrode assembly device as defined herein in a body of an implantee.

In this aspect, the method can comprise a step of accessing the implantation site and then a step of inserting the device. Prior to insertion, the device is preferably substantially straight or straight. On insertion, the device can adopt an intermediate configuration (as defined herein). Either prior to full insertion or following full insertion, the device preferably adopts its second configuration.

Once implanted, the electrodes can receive stimulation signals from a stimulator means. The stimulator means is preferably electrically connected to the elongate member by way of an electrical lead. The lead can include the one or more wires extending from each electrode of the array mounted on the elongate member.

In one embodiment, the lead can extend from the elongate member to the stimulator means or at least the housing thereof. In one embodiment, the lead is continuous with no electrical connectors, at least external the housing of the stimulator means, required to connect the wires extending from the electrodes to the stimulator means. One advantage of this arrangement is that there is no requirement for the surgeon implanting the device to make the necessary electrical connection between the wires extending from the electrodes and the stimulator means.

The stimulator means is preferably positioned within a housing that is implantable within the implantee. The housing for the stimulator means is preferably implantable within the bony well in the bone behind the ear posterior to the mastoid.

When implantable, the housing preferably contains, in addition to the stimulator means, a receiver means. The receiver means is preferably adapted to receive signals from a controller means. The controller means is, in use, preferably mounted external to the body of the implantee such that the signals are transmitted transcutaneously through the implantee.

Signals can preferably travel from the controller means to the receiver means and vice versa. The receiver means can include a receiver coil adapted to receive radio frequency (RF) signals from a corresponding transmitter coil worn externally of the body. The radio frequency signals can comprise frequency modulated (FM) signals. While described as a receiver coil, the receiver coil can preferably transmit signals to the transmitter coil which receives the signals.

The transmitter coil is preferably held in position adjacent the implanted location of the receiver coil by way of respective attractive magnets mounted centrally in, or at some other position relative to, the coils.

The external controller can comprise a speech processor adapted to receive signals output by a microphone. During use, the microphone is preferably worn on the pinna of the implantee, however, other suitable locations can be envisaged, such as a lapel of the implantee's clothing. The speech processor encodes the sound detected by the microphone into a sequence of electrical stimuli following given algorithms, such as algorithms already developed for cochlear implant systems. The encoded sequence is transferred to the implanted stimulator/receiver means using the transmitter and receiver coils. The implanted stimulator/receiver means demodulates the FM signals and allocates the electrical pulses to the appropriate attached electrode by an algorithm which is consistent with the chosen speech coding strategy.

The external controller further comprises a power supply. The power supply can comprise one or more rechargeable batteries. The transmitter and receiver coils are used to provide power via transcutaneous induction to the implanted stimulator/receiver means and the electrode array.

While the implant system can rely on external componentry, in another embodiment, the controller means, including the microphone, speech processor and power supply can also be implantable. In this embodiment, the controller means can be contained within a hermetically sealed housing or the housing used for the stimulator means.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An electrode assembly for an implantable hearing prosthesis comprising:
   an elongate member formed from a resiliently flexible material and having a plurality of electrodes mounted thereon;
   a tip disposed at a distal end of the elongate member, wherein the tip is less stiff than the elongate member;
   an elongate stiffening element; and
   a stiffening sheath configured to surround the tip, wherein the stiffening sheath is configured to dissolve and/or soften when exposed to cochlear fluids, and wherein the elongate member comprises a lumen configured to receive the elongate stiffening element.

2. The electrode assembly of claim 1, wherein the elongate member and the tip are separately formed, and wherein the tip is mounted to the distal end of the elongate member.

3. The electrode assembly of claim 1, wherein the tip is integrally formed with the elongate member.

4. The electrode assembly of claim 1, wherein the tip comprises a plurality of metallic particles substantially evenly dispersed through the tip.

5. The electrode assembly of claim 1, wherein the tip is solid.

6. The electrode assembly of claim 1, wherein the stiffening sheath is bioresorbable.

7. An electrode assembly for an implantable hearing prosthesis comprising:
   an elongate member formed from a resiliently flexible material and having a plurality of electrodes mounted thereon;
   a tip disposed at a distal end of the elongate member, wherein the tip is less stiff than the elongate member; and
   a stiffening sheath configured to surround the tip, wherein the stiffening sheath is stiffer than the tip,
   wherein the elongate member comprises a lumen terminating in an opening at the distal end of the elongate member, wherein the tip comprises a cavity having a opening at a proximal end of the tip that aligns with the lumen opening, and wherein the cavity is configured to receive a stiffening element extending beyond the lumen opening.

8. The electrode assembly of claim 7, wherein the stiffening element is stiffer than the tip.

9. An implantable tissue-stimulating device comprising:
an electrode assembly comprising:
- an elongate member formed from a resiliently flexible material and having a plurality of electrodes mounted thereon;
- a tip disposed at a distal end of the elongate member, wherein the tip is less stiff than the elongate member;
- an elongate stiffening element; and
- a stiffening sheath configured to surround the tip, wherein the stiffening sheath is configured to dissolve and/or soften when exposed to cochlear fluids, and wherein the elongate member comprises a lumen configured to receive the elongate stiffening element.

10. The device of claim 9, wherein the stiffness of the tip varies along a length of the tip.

11. The device of claim 9, wherein the stiffness of the tip is greater toward a proximal end of the tip than toward a distal end of the tip.

12. The device of claim 9, wherein the tip comprises:
a central core, wherein the core tapers toward a distal end of the tip, and extends less than an entire length between proximal and distal ends of the tip.

13. The device of claim 9, wherein the tip comprises:
a central core, wherein the core tapers toward the distal end of the tip.

14. The device of claim 13, wherein a central core extends less than an entire length between proximal and distal ends of the tip.

15. The device of claim 9, wherein the tip is formed at least in part from a bioresorbable material.

16. An implantable hearing prosthesis comprising:
an electrode assembly comprising:
- an elongate member formed from a resiliently flexible material and having a plurality of electrodes mounted thereon;
- a tip disposed at a distal end of the elongate member, wherein the tip is less stiff than the elongate member;
- an elongate stiffening element; and
- a stiffening sheath configured to surround the tip, wherein the stiffening sheath is configured to dissolve and/or soften when exposed to cochlear fluids, and wherein the elongate member comprises a lumen configured to receive the elongate stiffening element.

17. The hearing prosthesis of claim 16, wherein the elongate member comprises a lumen terminating in an opening at the distal end of the elongate member, wherein the tip comprises a cavity having a opening at a proximal end of the tip that aligns with the lumen opening, and wherein the cavity is configured to receive a stiffening element extending beyond the lumen opening.

18. The hearing prosthesis of claim 17, wherein the stiffening element is stiffer than the tip.

19. The hearing prosthesis of claim 16, wherein the tip is formed at least in part from a bioresorbable material.

20. The hearing prosthesis of claim 16, wherein the tip is formed at least in part from a polymeric material configured to become softer in the presence of moisture or body heat.

* * * * *